US006071505A

United States Patent [19]
Manuszak-Guerrini et al.

[11] Patent Number: 6,071,505
[45] Date of Patent: Jun. 6, 2000

[54] CATIONIC CELLULOSE DERIVATIVES OF CONTROLLED CHARGE DENSITY USEFUL IN COSMETIC PREPARATIONS

[75] Inventors: Melissa A. Manuszak-Guerrini, Baton Rouge, La.; Doris A. Culberson, Pensacola, Fla.; William H. Daly, Baton Rouge, La.

[73] Assignee: Board of Supervisors of Louisana State University and Agricultural and Mechanical College, Baton Rouge, La.

[21] Appl. No.: 09/286,814

[22] Filed: Apr. 6, 1999

Related U.S. Application Data

[62] Division of application No. 08/822,987, Mar. 21, 1997, Pat. No. 5,981,737
[60] Provisional application No. 60/172,241, Mar. 29, 1996.
[51] Int. Cl.[7] ............................. A61K 7/06; C07H 11/02; C07H 5/04; C08B 15/04
[52] U.S. Cl. .................... 424/70.28; 424/70.1; 536/18.7; 536/30; 536/56
[58] Field of Search ............................... 424/70.1, 70.28; 536/18.7, 30, 56

[56] References Cited

U.S. PATENT DOCUMENTS

| | | | |
|---|---|---|---|
| 4,415,552 | 11/1983 | Diener et al. | 424/91 |
| 4,988,806 | 1/1991 | Grüning et al. | 536/98 |
| 5,614,616 | 3/1997 | Buysch et al. | 536/44 |

OTHER PUBLICATIONS

Culberson, D. et al. "Approaches to the Synthesis of Aminoalkylcarbamoyl Cellulosics," Polym. Preprints, vol. 34, No. 1, pp. 564–565 (1993).
Culberson, D. et al., "A Study of the Complexation of Alkyl Sulfate Surfactants with Aminoalkylcarbamoyl Cellulosics," printed abstract and copy of slides given at oral presentation, Am. Chem. Soc. Meeting, Anaheim, CA (Apr. 1995).
Culberson, D. "Synthesis and Characterization of Aminoalkylcarbamoyl Cellulosics," pp.7–53, and 139–146, PhD Dissertation, Louisiana State University, Baton Rouge, LA (May 1995).
Culberson, D. et al., "Synthesis and Characterization of Aminoalkylcarbamoyl Cellulosics," Polym. Mat. Sci., vol. 71, pp. 498–499 (1994).
Manuszak–Guerrini, M.et al., "A Study of the Complexation of Aminoalkylcarbamoyl Cellulosics and Oppositely Charged Mixed Micelles," preprint of poster presentation, Society of Cosmetic Chemists National Meeting, New York, pp. 57–59 (Dec. 1995).
Manuszak–Guerrini, M. et al., "Structure Elucidation of Complexes of Aminoalkylcarbamoyl Cellulosics and Oppositely Charged Mixed Micelles," preprint of poster presentation submitted for Am. Chem. Soc. Mtg., New Orleans, LA (Mar. 24–27, 1996).
*Chem. Abstracts* 97:203224b (1982).
*Chem. Abstracts* 113:29109e (1989).
*Chem Abstracts* 112:160864u (1989).
*Chem. Abstracts* 112:200955h (1989).
*Chem. Abstracts* 115:282370n (1991).

*Primary Examiner*—Gary L. Kunz
*Assistant Examiner*—Everett White
*Attorney, Agent, or Firm*—John H. Runnels

[57] ABSTRACT

Water-soluble quaternary ammonium cellulosic derivatives of controlled charge density are disclosed. These derivatives are useful in cosmetic preparations, such as hair and skin formulations, for example hair conditioners. These quaternized cellulosic derivatives are useful as thickeners, conditioners, film formers, fixatives, emulsifiers, or additives in hair or skin formulations to improve combing, manageability, body, curl retention, moisture resistance, and binding of ingredients to keratin. Compared to existing agents, these compounds have improved temperature stability, improved interactions with surfactants (such as in shampoos), improved binding to keratin, improved mechanical properties, and can mend split ends on hair. A major advantage of these compounds is that they may be applied to hair directly from an aqueous solution, and do not require a volatile organic compound solvent as carrier. Alternatively, smaller amounts of VOC's may be used than is the case in current products, to improve drying times for the formulations. The compounds are also useful as antistatic agents, bactericides, flocculating agents, and as drug binding or drug delivery agents.

6 Claims, No Drawings

CATIONIC CELLULOSE DERIVATIVES OF CONTROLLED CHARGE DENSITY USEFUL IN COSMETIC PREPARATIONS

This is a divisional of co-pending application Ser. No. 08/822,987, filed Mar. 21, 1997; which claims the benefit of the Mar. 29, 1996 filing date of the provisional application that was originally filed as non-provisional application Ser. No. 08/623,675, and was later converted to provisional status.

This invention pertains to polymers that are useful in cosmetic preparations, particularly to cationic cellulose derivatives of controlled charge density that are useful in hair care preparations.

BACKGROUND OF THE INVENTION

Naturally-occurring polymers such as tragacanth, arabic, or karaya gums were used in early hair fixative products. These fixatives were typically delivered from either an aqueous or a hydroalcoholic medium onto damp hair. The hair was then styled and allowed to dry on rollers. This type of product was insufficient for all hairstyles, and an improved, quick drying product was developed, commonly known as hair spray.

Shellac was the first polymer used in hair sprays. Difficulties with shellac led to the use of synthetic resins instead—for example, polyvinylpyrrolidone (PVP), dimethylhydantoin formaldehyde (DMHF), PVP-vinyl acetate copolymer (PVP-VA), and polyvinylpyrrolidone-methylmethacrylate-methacrylic acid terpolymer. Ongoing efforts in the cosmetics industry to synthesize new polymeric resins have been driven by consumer demand for fixative products that are resistant to humidity, but that still may be removed easily upon shampooing.

The use of chlorofluorocarbons in hairsprays has been banned in the United States since 1979. Many hair fixatives are currently applied in a volatile organic compound ("VOC") carrier. As the use of VOC's becomes more restricted, there is an unfilled need for hair fixatives that may be applied with little or no VOC's. It would be desirable to devise a system in which water could replace some or all of the alcohol or propellant that is used in current formulations. Such a substitution presents a similar challenge to that faced by formulators over fifty years ago: how to produce a quick-drying fixative product that is resistant to humidity and that may be easily removed in an aqueous solution (e.g., shampoo). One way in which volatile solvents could be completely or partially replaced would be to use a water-soluble product whose affinity for hair exceeds its affinity for the aqueous solvent in which it is applied.

The principal component of hair is a protein called keratin. Three important factors in determining the binding of a polymer to keratin are: (1) the affinity of the polymer for keratin, (2) the strength of interactions of the polymer with the solvent phase, and (3) the diffusibility of the polymer into the hair. Polymer-keratin affinity is influenced by polymer charge, molecular size, isoelectric point of the hair, pH of the surrounding medium, formulation composition, and substituents attached to the surface of the keratin. The hydrophilicity or hydrophobicity of the polymer affects binding interactions with the aqueous phase. Diffusion into the fiber is controlled by the molecular size of the polymer, pH, reaction temperature, and the past history of the keratin (hysteresis).

Adsorption of a polymer onto keratin may be charge driven or hydrophobically driven. The adsorption process is a continuum between these two pathways, and can vary with changes in the pH or in the polymer structure. At low pH (pH<3.6), the adsorption of cationic polymers is hydrophobically driven as the pH is near or below the isoelectric point of hair. As pH increases above 3.6, the adsorption process becomes charge-driven as the negative charge of the hair fiber increases with increasing pH.

Bonding between polymers and keratin falls into three principal types: primary valence bonds (both ionic and covalent), polar interactions (especially hydrogen bonding), and van der Waals attractions. Cationic polymers in particular primarily bind to keratin through ionic bonds, enhanced by van der Waals forces. The strength of van der Waals bonding may approach that of ionic bonding, as the sum of individual van der Waals interactions increases with the number of repeat units in the polymer.

Polymeric quaternary ammonium salts ("polyquats") have been used for several purposes in cosmetic formulations due to their solubility in both aqueous and aqueous-alcoholic media. Polyquats have been used as thickeners, emulsifiers, fixatives, film formers, and additives in formulations to improve combing of hair, manageability, body, curl retention, and binding to keratin. Cationic ingredients tend to bind to hair keratin due to the low isoelectric point of hair (pH=3.67).

Prior polyquaternary ammonium cellulosic derivatives typically have a low degree of desorption from keratin, resulting in "buildup" or soiling of hair, and they can be resistant to removal by anionic surfactants. These problems have limited their use. Prior polyquaternary ammonium cellulosic derivatives have had low solubility in water, requiring the use of high levels of volatile organic compounds in many hair formulations. Current environmental regulations require the reduction of volatile organic compounds, making the long-term use of prior polyquaternary ammonium cellulosic derivatives impractical for many applications.

Cellulose. Cellulose, a major component of most terrestrial plants, is a polymer formed of repeating $\beta$-1,4 D-glucose units ("anhydroglucose units."). Numerous hydroxyl groups on cellulose participate in extensive intra- and inter-molecular hydrogen bonding, making cellulose a stiff, rod-like polymer. Reactions with cellulose generally require initial activation of the hydroxyl groups to enhance nucleophilicity.

The applications and properties of cellulose derivatives are greatly influenced by the degree of substitution along the cellulose chain. The "degree of substitution" is defined as the average number of hydroxyl groups that have been substituted per anhydroglucose unit in the polymeric backbone. Each anhydroglucose unit has three hydroxyl groups, located at the C2, C3, C6 positions. The C2 and C3 positions are secondary alcohols, and C6 is a primary alcohol. The three hydroxyl groups exhibit different rates of reactivity to different reagents. In an etherification reaction, the order of reactivity is C2>C6>C3.

Cellulose ethers are generally soluble in water or common organic solvents. They can be prepared by nucleophilic substitution reactions under alkaline conditions. The most important commercially available cellulose ethers, such as carboxymethyl cellulose (CMC), methylcellulose (MC), hydroxyethyl cellulose (HEC), and hydroxypropyl cellulose (HPC) are prepared by this method. The Michael addition is used to prepare cyanoethylated cellulose or carbamoyl cellulose by treating cellulose with acrylonitrile or acrylamide, respectively. Cellulose ethers are used as thickeners, flow control agents, suspending agents, protective colloids, films, and thermoplastics. Cellulose ethers are generally nontoxic to humans, animals, and ecological systems.

Amino Cellulose Derivatives The introduction of amino groups onto cellulose molecules increases reactivity by forming a cellulosate "macroinitiator." that is suitable for further derivatisation. Amino cellulosics have been used as immunoadsorbents, in enzyme immobilization, as ion-exchange resins, and as macroinitiators for vinyl monomers.

The preparation of primary aminoalkyl cellulosics generally involves reacting activated cellulose with aminoalkyl halides, aminoalkylsulfuric acid, or ethylenimine. Another method to prepare aminoalkyl cellulosics involves the direct reduction of the nitrile group of cyanoethylated cellulose to give aminopropyl cellulose. The Hofmann rearrangement of carbamoylethylcellulose with $Br_2$/NaOH for 30–120 min also gives aminopropyl cellulose. Reacting activated cellulose with epichlorohydrin, followed by subsequent reaction with various diamines gives O-[2-Hydroxy-3-($\omega$(-aminoalkylamino) propyl cellulose. Cellulose acetate may be treated with sodium naphthalene in tetrahydrofuran to prepare the sodium cellulosate initiator. The sodium cellulosate initiator can then react with the N-carboxy anhydride derivative of D,L phenylalanine, $\gamma$-benzyl-L-glutamate, s-benzyl-L-cysteine, or sarcosine to yield single aminoacid cellulose derivatives, without forming polypeptide graft copolymers.

Aminocarbamoyl Cellulosics. A water soluble 2-aminoethyl-carbamoyl cellulose with a low degree substitution (DS$\leq$0.02) may be prepared by treating sodium carboxymethyl cellulose with excess ethylenediamine in the presence of water soluble carbodiimides.

Converting carboxymethyl cellulose to an alkyl ester produces a derivative more receptive to aminolysis, thus increasing the degree of substitution. For example, reacting carboxymethyl cellulose ("CMC") (DS>0.1) with methyl chloride at 100° C. yields methyl carboxymethylcellulose ester. Reacting this ester with various diamines in methanol at 150° C. for 1 hour yields aminoamide cellulosics. The aminoamide cellulosics may be quaternized by treatment with methylchloride in methanol at room temperature. The quaternized derivatives had a degree of substitution of 0.67. Betainized cellulose derivatives are prepared after treating the aminoamide cellulosics with $Cl(CH_2)_yCO_2Na$ in isopropanol at 60° C. for 6 hours. The quaternized and betainized cellulosics (DS=0.63) can be applied as hair bleaches and shampoos.

Hydroxyethylcellulose was treated with the betainization reagent prepared by heating a mixture of dimethylglycine, isopropanol, and epichlorohydrin at 50° C. The betainized cellulose improved the feel and combing capacity of hair. The CMC ester may be prepared by treating the CMC salt (DS=1) with dimethylsulfate in isopropanol at 25° C. for 2 hours and 70° C. for 2 hours. The CMC ester is treated with various diamines in toluene at 100° C. for 5 hours, giving aminoamides with a DS of 0.7. The quaternized derivatives have been used to flocculate china clay suspensions.

U.S. Pat. No. 4,988,806 discloses certain aminoalkylcarbamoylmethyl cellulosics, certain monoquaternary ammoniumalkylcarbamoylmethyl cellulosics, and their use in cosmetic preparations.

U.S. Pat. No. 4,415,552 discloses aminoalkylcarbamoylmethyl cellulosics said to be useful as non-immunogenic carriers for allergenic haptens, to help establish immunological tolerance to those haptens. See also Chem. Abstracts 97:203224b (1982).

D. Culberson et al., "Approaches to the Synthesis of Aminoalkylcarbamoyl Cellulosics," Polym. Preprints, vol. 34, no. 1, pp. 564–565 (1993); and D. Culberson et al., "Synthesis and Characterization of Aminoalkylcarbamoyl Cellulosics," Polym. Mat. Sci., vol. 71, pp. 498–499 (1994) disclose the synthesis and characterization of aminopropyl amidocarboxyethyl cellulose, certain aminoalkyl carboxyamidomethyl celluloses, and certain poly quaternary ammonium salts.

D. Culberson et al., "A Study of the Complexation of Alkyl Sulfate Surfactants with Aminoalkylcarbamoyl Cellulosics," printed abstract and copy of slides given at oral presentation, Am. Chem. Soc. Meeting, Anaheim, CA (April 1995) discloses phase diagrams of mixtures of aqueous surfactants with certain aminoalkylcarbamoyl cellulosics.

M. Manuszak-Guerrini et al., "A Study of the Complexation of Aminoalkylcarbamoyl Cellulosics and Oppositely Charged Mixed Micelles," preprint of oral presentation, Society of Cosmetic Chemists National Meeting, New York, pp. 57–59 (December 1995) discloses measurements on the interaction of certain aminoalkylcarbamoyl graft copolymers with sodium dodecyl sulfate-octoxynol mixed micelles. See also M. Manuszak-Guerrini et al., "Structure Elucidation of Complexes of Aminoalkylcarbamoyl Cellulosics and Oppositely Charged Mixed Micelles," preprint of poster presentation submitted for Am. Chem. Soc. Mtg., New Orleans, La. (Mar. 24–27, 1996).

D. Culberson, "Synthesis and Characterization of Aminoalkylcarbamoyl Cellulosics," pp. 7–53, and 139–146, PhD Dissertation, Louisiana State University, Baton Rouge, La. (May 1995) discloses the synthesis and characterization of a number of aminoalkylcarbamoyl cellulosics.

Certain polysaccharide derivatives for use in hair, cosmetic, and flocculating compositions are disclosed in Chem. Abstracts 113:29109e (1989); Chem. Abstracts 112:160864u (1989); Chem. Abstracts 112:200955h (1989); and Chem. Abstracts 115:282370n (1991).

SUMMARY OF THE INVENTION

Novel water-soluble quaternary ammonium cellulosic derivatives of controlled charge density have been discovered. These derivatives are useful in cosmetic preparations, such as hair and skin formulations, particularly as hair conditioners.

These quaternized cellulosic derivatives are useful as thickeners, conditioners, film formers, fixatives, emulsifiers, or additives in hair or skin formulations to improve combing, manageability, body, curl retention, moisture resistance, and binding of ingredients to keratin. Compared to existing agents, the novel compounds have improved temperature stability, improved interactions with surfactants (such as in shampoos), improved binding to keratin, improved mechanical properties, and can mend split ends on hair. A major advantage of the novel compounds is that they may be applied to hair directly from an aqueous solution, and do not require a volatile organic compound solvent as carrier. Alternatively, smaller amounts of VOC's may be used than is the case in current products, to improve drying times for the formulations.

The novel compounds are also useful as antistatic agents, bactericides, flocculating agents, and as drug binding or drug delivery agents.

A monoquaternary ammonium cellulosic derivative may be illustrated schematically as:

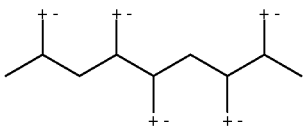

A diquaternary ammonium cellulosic derivative may be illustrated schematically as:

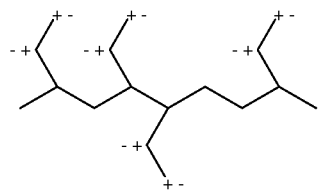

A polyquaternary ammonium cellulosic derivative may be illustrated schematically as:

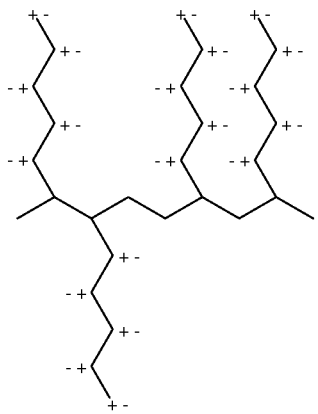

More particularly, diquats in accordance with the present invention are derivatives of carboxymethyl cellulose in which some or all of the carboxymethyl groups are replaced by diquaternary ammonium groups of the general formula

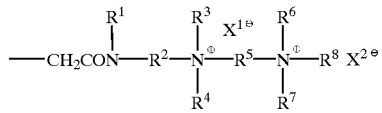

wherein there are at least about 0.2 such diquaternary ammonium groups present for each anhydroglucose unit of the polymeric molecule, preferably between about 0.3 and about 0.7 diquaternary groups per anhydroglucose unit, most preferably about 0.5; and wherein:

$R^1$ is hydrogen or methyl, preferably hydrogen.

$R^2$ is a divalent aliphatic hydrocarbon group with 2 to 20 carbon atoms, preferably —$CH_2$—$CH_2$— or —$CH_2$—$CH_2$—$CH_2$—.

$R^3$, $R^4$, $R^6$, $R^7$, and $R^8$ are alkyl groups with 1 to 4 carbon atoms that may be the same as one another or different from one another, and are preferably each methyl groups.

$R^5$ is a substituted or unsubstituted divalent aliphatic group with 2 to 5 carbon atoms, preferably —$CH_2$—CH(OH)—$CH_2$—.

$X^1$ and $X^2$ are anions that may be the same as one another or different from one another; preferably a halide, a sulfate ester group, or a sulfonic acid group, most preferably chloride.

Polyquats in accordance with the present invention are derivatives of carboxymethyl cellulose in which some or all of the carboxymethyl groups are replaced by polyquaternary ammonium groups of the general formula

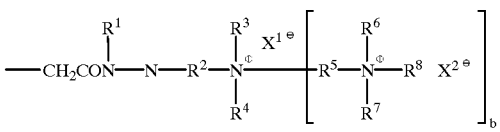

wherein there are at least about 0.2 such polyquaternary ammonium groups present for each anhydroglucose unit of the polymeric molecule, preferably between about 0.3 and about 0.7 diquaternary groups per anhydroglucose unit, most preferably about 0.5; wherein b is between 2 and 8, preferably 4 or 5; and wherein:

$R^1$ is hydrogen or methyl, preferably hydrogen.

$R^2$ is a divalent aliphatic hydrocarbon group with 2 to 20 carbon atoms, preferably —$CH_2$—$CH_2$— or —$CH_2$—$CH_2$—$CH_2$—.

$R^3$, $R^4$, $R^6$, $R^7$, and $R^8$ are alkyl groups with 1 to 4 carbon atoms that may be the same as one another or different from one another, and are preferably each methyl groups.

$R^5$ is a substituted or unsubstituted divalent aliphatic group with 2 to 5 carbon atoms, preferably —$CH_2$—CH(OH)—$CH_2$—.

$X^1$ and $X^2$ are anions that may be the same as one another or different from one another; preferably a halide, a sulfate ester group, or a sulfonic acid group, most preferably chloride.

Water soluble aminoamides were obtained, for example, by reacting methyl carboxymethyl cellulose with an excess of diamines, $NH_2(CH_2)_xNR'R''$, where x is typically 2 or 3, and R', R'' are typically H or $CH_3$. These derivatives were then quaternized with iodomethane and a catalytic amount of iodine to obtain monoquaternary salts. Alternatively, the aminoamide cellulosics were treated with N-(3-chloro-2-hydroxypropyl) trimethyl ammonium chloride to yield diquaternary cellulosic derivatives. As another alternative, polyquaternary ammonium cellulosics were prepared by reacting the aminoamides with epichlorohydrin and dimethylamine.

DESCRIPTION OF PREFERRED EMBODIMENTS

Synthesis of Aminoalkylcarbamoylmethyl Cellulosics

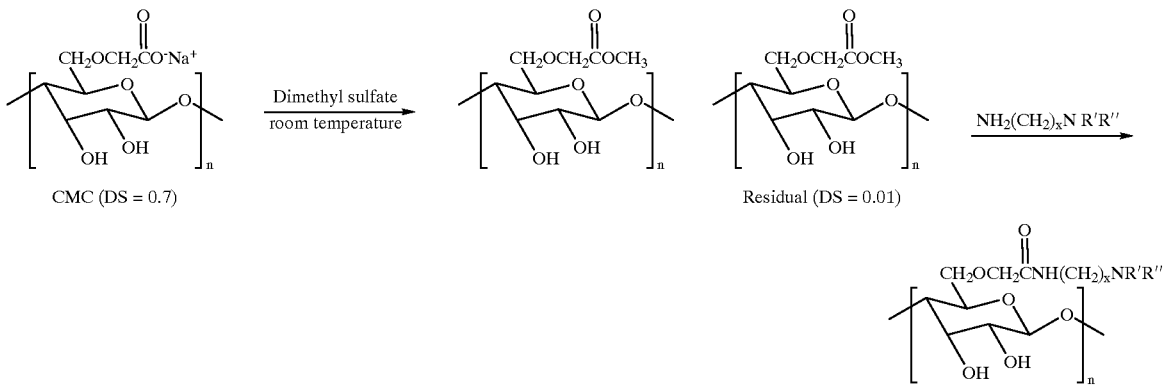

Sodium carboxymethyl cellulose was readily converted to a water-insoluble methyl carboxymethyl cellulose ("MCMC") by a direct displacement reaction with dimethyl sulfate. The reaction has been conducted both in neat dimethyl sulfate and in DMSO solution. In either case an insoluble ester, MCMC, was obtained. The MCMC reacts under homogeneous conditions with neat diamines to produce water soluble CMC amides. See Table 1.

TABLE 1

| Run | Diamine | MCMC, (g) | Yield, g (%) |
|---|---|---|---|
| CMCED | ethylene diamine | 2.14 | 1.84 (86%) |
| CMCNNED | N,N-dimethyl-ethylene diamine | 2.05 | 1.98 (97%) |
| CMC13DAP | 1,3-diamino-propane | 2.07 | 1.58 (76%) |
| CMCJ148 | Jeffamine 148 | 1.03 | 0.81 (79%) |

The abbreviations used above are as follows:
CMCED = aminoethylcarbamoyl methyl cellulose
CMCNNED = N,N-dimethylaminoethylcarbamoyl methyl cellulose
CMC13DAP = aminopropylcarbamoyl methyl cellulose
CMCJ148 = carbamoylmethyl cellulose-g-co-(polyoxyethylene)-amine The conversion of the CMC salt to aminoamides via methyl carboxymethyl cellulose (MCMC) was confirmed by Fourier transform infrared spectroscopy ("FTIR"). The carbonyl absorption shifted from 1606 cm$^{-1}$ (CMC) to 1746 cm$^{-1}$ (MCMC), and finally to 1596 cm$^{-1}$ (CMC amide). The appearance of amide I and II bands at 1660 and 1578 cm$^{-1}$ confirmed the amid ation of the CMC ester. Analysis of the $^1$H NMR spectra showed the presence of positional isomers, arising from amidation at the C2 and C6 positions on the glucose ring. The anhydroglucose ring protons appeared as a broad peak, 3.254–4.50 ppm. The alkyl substituent protons appeared from 2.40–3.24 ppm. Analysis of the $^{13}$C NMR spectra showed the presence of the anhydroglucose ring carbons C1 and C6 at 105.0 ppm and 60.0 ppm, respectively, and the C2–C5 carbons overlapping from 70.0–85.0 ppm. The amide carbonyl was also present at 177.0 ppm.

The degree of amidation, shown in Table 2, was determined using a modified ASTM method for carboxymethylcellulose (sodium salt), and by elemental analysis. The aminoamide derivatives were dried and refluxed in glacial acetic acid for 2.5 hrs and allowed to cool. The solutions were titrated conductrimetrically with perchloric acid and dioxane. The residual salts of the aminoamide derivatives after titration with perchloric acid/dioxane were not water soluble, nor were the acetate salts formed during reflux in acetic acid. However, the salts were slightly soluble in DMSO/H$_2$O. High degrees of substitution were generally obtained, except for decreased substitution with N,N'1,2-dimethylethylene diamine (CMCSED) (DS=0.35) and 1,2 diaminopropane (DS=0.37), attributed to steric effects. The degree of amidation calculated from elemental analysis was in close agreement to the DS calculated by titration. In Table 2, the figures in parentheses are calculated from the nitrogen content of the polymers based on elemental analysis.

TABLE 2

Degree of Amidation and Intrinsic Viscosity

| Derivatives | DS (titration) | meq/g (titration) | $\eta = \eta_{sp}/c$ |
|---|---|---|---|
| CMCED | .49 | 1.68 | 3.95 |
| CMCNNED | .56 | 1.77 | 2.37 |
| CMC13DAP | .51 | 1.70 | 2.44 |
| CMCJ148 | .65 | 1.79 | |
| CMCNNED | .57 (.51) | 2.64 (3.26) | 3.90 |
| CMCNNDAP | .66 (.57) | 2.81 (3.54) | 1.08 |

Abbreviations used above:
CMCNNDAP = N,N-dimethylaminopropylcarbamoylmethyl cellulose
MCMC = methyl carboxymethyl cellulose ester Reactivity of the Amino Functional Group To confirm that the amino end groups were accessible to further modification, cross-linking of the aminoamide derivatives in Table 2 with excess epichlorohydrin under heterogeneous conditions at 70° C. was performed.

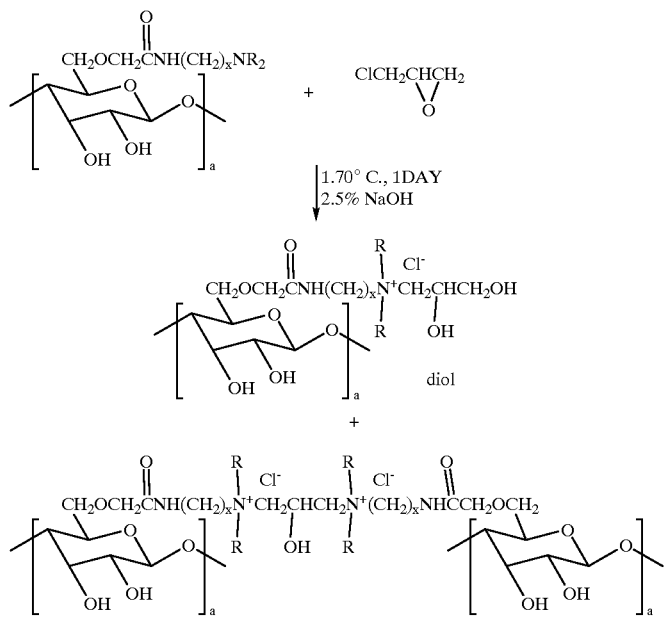

The amino functional group initiated a nucleophilic attack on the epichlorohydrin, and subsequent displacement of the chloride by the intermediate alkoxide ion reformed the epoxide derivative at room temperature. The mixtures were washed with acetone and dried under vacuum. The extent of reaction was estimated by the weight of product isolated (Table 3).

TABLE 3

Reactivity of Amino Functional Group

| Derivatives | sample (g) | epichlorohydrin (ml) | conditions | yield (g) |
|---|---|---|---|---|
| CMCED | 0.1078 | 10 | 70° C., overnight | .0958 |
| CMCNNED | 0.1285 | 10 | 70° C., overnight | .1114 |
| CMC13DAP | 0.1750 | 10 | 70° C., overnight | .1556 |
| CMCNNDAP | 0.1020 | 10 | 70° C., overnight | .0866 |

The derivatives were placed in distilled water; no dissolution occurred. Upon addition of 1% or 5% NaOH, the aminoamides prepared from N,N'-dimethylalkylenediamines dissolved over a period of three days at room temperature. Dissolution occurred because a nucleophilic attack by the hydroxide opened the epoxide ring, forming the diol product. $^1$H NMR confirmed the ring-opening of the aminoamide epoxide intermediate to the ring-opened diol aminoamide derivative. The aminoamides prepared from the unsubstituted diaminoalkanes formed predominantly cross-linked networks that were partially soluble under basic conditions. The difference in the reactivity of the amino functional groups was clearly related to steric factors. The more sterically crowded tertiary amino end groups stopped at the epoxide intermediate, whereas the less hindered primary amino end groups formed the cross-linked networks.

Thermal Analysis. A differential scanning calorimetry trace of the MCMC ester showed two transitions, a $T_{M1}$, 90.3° C. and a Td (exothermic), 300.1° C. (Table 4). Amidation lowered $T_{M1}$, 90.3° C., by ~20–30° C. for the aminoamide cellulosics. The DSC traces showed a possible Tg at ~12° C., and the onset of the broad melt transition, $T_{M1}$, at ~68° C. The shift to a lower $T_{M1}$ was attributed to side chain mobility. An additional transition, not observed in MCMC ester, appeared at 207.8° C., 206° C., and 213.4° C. for the CMCNNED, CMC13DAP, and CMCNNDAP aminoamide cellulosics, respectively. This transition was attributed to the loss of the side chain. The decomposition temperature $T_d$ was only mildly effected by amidation. CMCNNED and CMCNNDAP showed a small increase in $T_d$, while CMCED and CMC13DAP showed a small decrease in $T_d$. (All samples were initially heated to a 130° C. to remove any absorbed water.)

Typically, the temperature of onset of major weight loss for unmodified cellulose is between 270–300° C. In general, purification by bleaching and scouring raises this onset temperature, while chemical modifications such as tosylation, cyanoethylation, disulfide crosslinking, thioacetylation, benzhydrylation, and tritylation tend to lower the decomposition temperature of cellulose.

TABLE 4

Comparison of the DSC Transitional Temperatures for Aminoalkylcarbamoylmethyl cellulosics

| Derivatives | $T_{M1}$ | $T_{M2}$ | T | $T_d$ (exo)[a] |
|---|---|---|---|---|
| MCMC | 90.3 | | 233.3 | 300.1 |
| CMCED | 59.6 | | 253.9 | 287.5 |
| CMCNNED | 79.1 | 207.8 | 262.9 | 307.1 |
| CMC13DAP | 81.9 | 206.4 | 263.1 | 293.1 |
| CMCNNDAP | 68.0 | 213.4 | 261.3 | 302.9 |

(a) Exothermic decomposition temperature.

The modified celluloses, CMC salt and MCMC ester, showed a decrease in the onset of thermal decomposition at 264.4° C. and 244° C. C.($T_{d2}$) respectively (Table 5). Interestingly, the amidation of the MCMC ester increased the thermal stability of the modified cellulose to a thermal decomposition temperature slightly higher than that of CMC salt. For the aminoamide cellulosic TGA traces, the first observable weight loss for the aminoamide cellulosics occurred between 264.4° C. and 271.9° C. ($T_{d2}$); weight loss then accelerated to an inflection point near 293.9–305.5° C. ($T_{d3}$), and leveled off between 316.0° C. and 333.7° C. ($T_{d4}$). The DTA traces did show an endotherm associated with the formation and volatilization of levoglucosan at 278.2° C. (CMC), 307.6° C. (MCMC), 295.0° C (CMCNNDAP), 299.2° C. (CMCNNED), and 286.6° C. (CMCED and CMC13DAP). The aminoamides containing primary amino end groups on their side chains, CMCED and CMC13DAP, showed an initial weight loss, $T_{d1}$, that was not observed for the starting materials, CMC salt and MCMC, or for CMCNNED and CMCNNDAP. This initial weight loss was attributed to "bound" water that was tightly held through hydrogen bonding with the primary amino groups, and that was not driven off by the initial heating to 130° C.

TABLE 5

Comparison of TGA Decomposition Temperatures of Aminoalkylcarbamoylmethyl cellulosics

| Derivatives | $T_{d1}$ | $T_{d2}$ | $T_{d3}$ | $T_{d4}$ | char at 500° C. |
|---|---|---|---|---|---|
| CMC | | 264.4 (11.3%) | 276.1 (25.5%) | 288.3 (51.5%) | 39.1% |
| MCMC | | 244.5 (14.1%) | 301.3 (37.6%) | 345.8 (58.9%) | 33.0% |
| CMCED | 132.1 (10.2%) | 268.2 (18.0%) | 293.9 (42.7%) | 316.0 (60.8%) | 27.4% |
| CMCNNED | | 271.9 (15.2%) | 305.5 (47.2%) | 336.0 (76.1%) | 16.4% |
| CMC13DAP | 168.8 (11.6%) | 265.3 (19.7%) | 295.0 (44.7%) | 323.0 (66.2%) | 19.7% |
| CMCNNDAP | | 265.3 (14.6%) | 304.5 (48.6%) | 333.7 (74.4%) | 16.3% |

(1) The percentages in parentheses denote percentage loss of material at that temperature.
(2) The char percentage is the amount of char remaining at 500° C.

Synthesis of Cationic Cellulosic Quaternary Ammonium Salts ("Monoquats"). The quarternary ammonium salts ("monoquats") were readily prepared from the aminoamide derivatives by slurrying in iodomethane with a small amount of iodine catalyst at room temperature for 3 days (Table 6). The aminoamides were purified by washing in acetone and drying under vacuum.

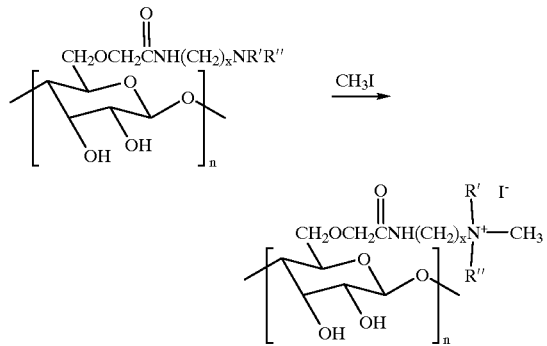

The discovery that iodine catalyzes the above reaction was serendipitous. This reaction was originally performed with iodomethane from an older jar of that reagent, without intentionally added catalyst. The reaction proceeded as depicted above. But when the reaction was repeated with reagent taken from a newer jar of iodomethane, the reaction did not occur. Investigation revealed that the difference was that the "old" iodomethane incorporated a small amount of elemental iodine as a breakdown product, while the "new" iodomethane did not. Adding a small amount of $I_2$ to the "new" $CH_3I$ caused the reaction to proceed successfully.

TABLE 6

Preparation of Monoquats

| Derivatives | sample (g) | yield (g) |
|---|---|---|
| MQNNED | 1.03 | 1.10 |
| MQ13DAP | 0.42 | 0.54 |
| MQNNDAP | 1.02 | 1.10 |

Abbreviations used above:
MQNNED = trimethylammonium methyl carbamoylmethyl cellulose chloride
MQ13DAP = trimethylammonium propyl carbamoylmethyl cellulose chloride
MQNNDAP = methylammonium propyl carbamoylmethyl cellulose chloride Resulting cationic charge densities are shown in Table 13 below. The hydrogen chloride derivatives of the aminoamides were prepared by strongly acidifying the solutions prior to titration with potassium polyvinylsulfate, (PVSK) (Table 10 below).

Synthesis of Diquaternary Ammonium Salts ("Diquats"). The quaternizing agent Quat 188 (Dow Chemical) is a 65% aqueous solution of N(-3-chloro-2-hydroxypropyl) trimethylammonium chloride:

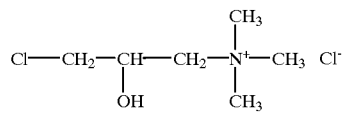

The quaternization of the aminoamide cellulosics occurs through the more reactive epoxidized Quat 188. The epoxidized derivative is formed in situ upon addition of NaOH:

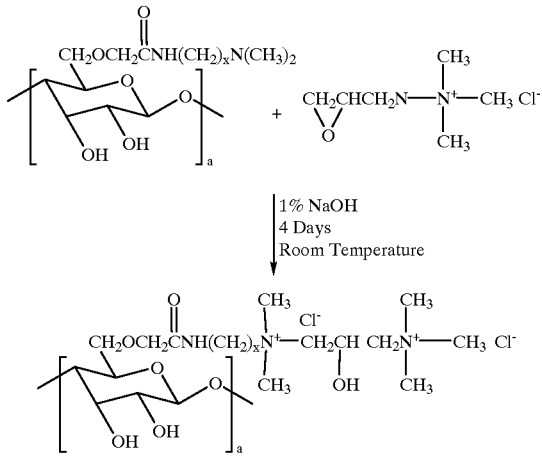

In this synthetic scheme, note that the value of "x" may readily be manipulated to alter the extension of the side groups attached from the cellulosic backbone. A preferred value for "x" is 2 or 3.

The aminoamide cellulosics were dissolved in 1% NaOH (Table 7) or 10% NaOH (Table 8), and then 10 ml of Quat 188 1.15 was added. The solutions were allowed to react for 4 days at room temperature, dialyzed for 3 days against distilled, deionized water, and then freeze-dried. The NaOH solution (1% or 10%), was used both as a solvent for the aminoamides, and as a reagent to epoxidize the Quat 188.

The amino functional group attacked the epoxidized Quat 188 to form the diquats. Analysis of the $^1$H NMR confirmed the addition of Quat 188 to the aminoamide cellulosics.

TABLE 7

Preparation of Diquats with 1% NaOH

| derivatives | sample (g) | Q188 (ml) | NaOH (1%) (ml) | yield (g) |
|---|---|---|---|---|
| DQED | 0.1072 | 10.0 | 10.0 | 0.1611 |
| DQNNED | 0.2655 | 10.0 | 10.0 | 0.2872 |
| DQ13DAP | 0.1767 | 10.0 | 10.0 | 0.2048 |
| DQNNDAP | 0.1060 | 10.0 | 10.0 | 0.1374 |

Abbreviations used above:
DQED = trimethylammonium-2-hydroxypropyl-N-ammoniumethyl carbamoylmethyl cellulose chloride
DQNNED = trimethylammonium-2-hydroxypropyl-N,N-dimethylammoniumethyl carbamoylmethyl cellulose chloride
DQ13DAP = trimethylammonium-2-hydroxypropyl-ammoniumpropyl carbamoylmethyl cellulose chloride
DQNNDAP = trimethylammonium-2-hydroxypropyl-N,N-dimethylammoniumpropyl carbamoylmethyl cellulose chloride

TABLE 8

Preparation of Diquats with 10% NaOH

| derivative | sample (g) | Q188 (ml) | NaOH (10%) (ml) | yield (g) |
|---|---|---|---|---|
| DQNNED | 2.01 | 10.0 | 10.0 | 2.33 |
| DQ13DAP | 0.63 | 10.0 | 10.0 | 0.79 |
| DQNNDAP | 0.80 | 10.0 | 10.0 | 0.54 |

Synthesis of Polyquaternary Ammonium Salts (Polyquats). Polyquaternary ammonium salt copolymers were prepared by reacting aminoamide cellulosics with epichlorohydrin and dimethylamine as shown (Table 9):

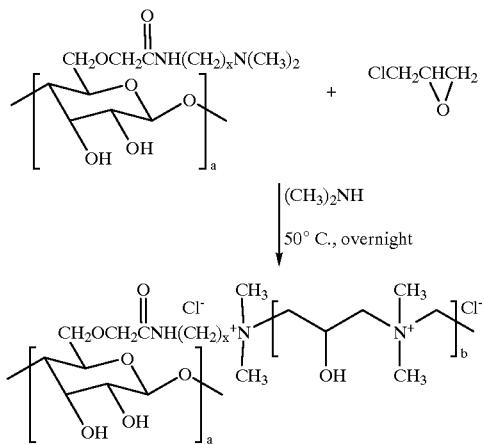

As for the diquats, the value of "x" may readily be manipulated to alter the size of the side chains. The value of "b" may also readily be manipulated to alter the charge density. Typical values of "b" are 4 or 5.

The aminoamides cellulosics CMCNNED and CMCNNDAP have tertiary amino terminal groups on the side chains. The nucleophilic attack of the tertiary amino groups on epichlorohydrin gave an intermediate containing a quaternary ammonium salt and an a epoxide. The more reactive dimethylamine could then attack the epoxide, opening the ring, thus continuing the nucleophilic addition of the epichlorohydrin and dimethylamine. Analysis of the $^1$H NMR showed broad overlapping peaks. A comparison of $^{13}$C NMR analysis of the starting aminoamide cellulosics to the polyquat showed additional carbon signals in the all region of the spectra, corresponding to the quaternized derivative.

TABLE 9

Preparation of Polyquats

| Derivatives | sample (g) | dimethyl-amine (ml) | epichlorohydrin (ml) | time | yield (g) |
|---|---|---|---|---|---|
| PQNNED[a] | 0.4396 | 10.0 | 1.0 | 1 day | 0.9733 |
| PQNNDAP[b] | 0.5356 | 25.0 | 15.0 | 3 days | 1.4063 |
| PQNNED[a] | 0.6100 | 10.0 | 5.0 | 1 hr. | |
| PQNNDAP[b] | 0.1840 | 16.0 | 17.0 | 3 days | 1.5747 |

[a] The product was precipitated in acetone and dried under vacuum.
[b] The product was dialyzed and freeze-dried.
Abbreviations used above:
PQNNDAP = N,N-dimethylammoniumpropyl carbamoylmethylcellulose-g-co (poly-N'-3-trimethylammonium-2-hydroxypropyl) chloride
PQNNED = N,N-dimethylammoniumethyl carbamoylmethyl cellulose-g-co (poly-N'-3-trimethylammonium-2-hydroxypropyl) chloride Determination of Cationic Charge Density. In conventional analyses of polyelectrolytes, the anionic or cationic colloid is typically titrated with either polydiallyldimethylammonium chloride (DADMAC) or potassium polyvinylsulfate (PVSK), respectively. The endpoint is determined by the color change of toluidine blue indicator from blue to red-wine. Conductimetric, turbidimetric, and iodine ion selective electrode methods have also been used to analyze polyelectrolytes. More recent methods for determining charge density include fluorescent indicators such as 6-(p-toluidino)-2-naphthalenesulfonic acid, potassium salt (TNS); 8-anilino-1-naphthalenesulfonic, ammonium salt (ANS); acridine orange; acriflavine hydrochloride; and safranine O to directly titrate anionic and cationic polyelectrolytes with $10^{-4}$ standard solutions of DADMAC and PVSK. The unbound dyes are practically nonfluorescent but exhibit strong fluorescence when bound to a polyelectrolyte. The fluorescence intensity of the polyelectrolyte-dye complex diminishes when titrated with a standard solution of PVSK or DADMAC. During the titration with PVSK or DADMAC the dye is liberated and is substituted with the PVSK or DADMAC. The fluorescence intensity becomes constant after the endpoint is reached.

The aminoamide derivatives were quaternized to different degrees of quaternization: mono., di-, and polyquaternization. Turbidimetric and indicator methods proved to be most effective in analyzing the quaternized aminoamide cellulosics. Sodium dodecyl sulfate (SDS) and PVSK were standardized with cetylpyridinium chloride monohydrate (CPM). The quaternized cellulosics were dissolved in distilled water. Aliquots of the solutions were titrated using PVSK or SDS with continuous stirring and pH monitoring. The pH was adjusted as needed with HCl or NaOH solutions. The turbidity and indicator methods were performed simultaneously by adding 2 drops of toluidine blue indicator to the sample. Aliquots of the sample were pipetted into cuvettes, and the turbidity was monitored as percent transmittance. A titration curve of transmittance vs. volume of titrant was plotted, and the endpoint was determined as the inflection point. The indicator color changed from blue to red-wine. An initial reduction in transmittance at 600 nm was observed due to the presence of the indicator. A reduction in transmittance at 520 nm increased in intensity as the observed equivalence point was detected by the color change. However, the toluidine blue indicator was not effective for titrations using SDS: At the presumed equivalence point there was no color change. However, the solutions did become turbid, and the turbidity method was suitable for turbidimetric analysis of the polyelectrolytes.

The cellulosic aminoamides were treated with HCl at room temperature to yield cellulosic ammonium amide hydrogen chlorides. The pH (2.5) was maintained by adjustment with HCl and NaOH as needed. The charge per gram (meq/g), determined by the turbidimetric method, was approximately half that determined by the conductimetric method (Table 10). The discrepancy in the measurements was attributed to two factors: (1) titrant diffusion through the media, and (2) quaternization of the amino end group. In the conductimetric method, the cellulosic aminoamides were refluxed in acetic acid to quaternize the amino moiety, whereas quaternization with HCl at room temperature was used for the turbidity method. Both techniques relied on diffusion of the titrant to complex with the poly-ion. Perchloric acid was the titrant in the conductimetric method, which involved complexation with the acetate ion. The turbidity method required the complexation of two polymers (PVSK and titrant) with the charged cellulosic aminoamide for precipitation to occur.

The diquats (1% NaOH) were analyzed with both the toluidine blue indicator and the turbidity method. The diquats were dissolved in distilled water, and 2 drops of indicator were added. The derivatives were titrated with PVSK to the indicator endpoint, blue to red-wine. Hydrochloric acid was added and the pH adjusted to 2.5. The titration was continued with the PVSK to the turbidimetric endpoint. The extent of quaternization for the diquats prepared with 1% NaOH was less than 0.1 for all the derivatives (Table 11). Upon acidification, the unreacted amino groups were quaternized and the extent of quaternization was then close to that of the cellulosic ammonium amide hydrochlorides (Table 12).

The quaternization of diquats prepared with 10% NaOH was also determined by the indicator and turbidity methods. The concentration of base affected the extent of quaternization substantially. Compare Table 11 with Table 14.

TABLE 10

Turbidimetric Titration of Monoquat Hydrogen chlorides

| Derivatives | mg of sample | ml of PVSK | meq/g |
| --- | --- | --- | --- |
| MQED | 4.13 | 23.0 | 1.15 |
| MQNNED | 6.20 | 19.5 | 0.65 |
| MQ13DAP | 2.76 | 11.0 | 0.82 |
| MQNNDAP | 4.34 | 15.5 | 0.74 |

$N = 2.06 \times 10^{-4}$ eq/l; pH = 2.5

TABLE 11

Determination of Cationic Charge for Diquats* at pH = 6.0

| Derivatives | mg of sample | ml of PVSK | meq/g (Indicator) |
| --- | --- | --- | --- |
| DQED | 3.72 | 0.4 | 0.022 |
| DQNNED | 3.67 | 1.2 | 0.067 |
| DQ13DAP | 3.99 | 0.9 | 0.046 |
| DQNNDAP | 3.61 | 1.4 | 0.080 |

(1) $N = 2.06 \times 10^{-4}$ eq/l; pH = 6.0
(2)* Diquats prepared with 1% NaOH.

TABLE 12

Determination of Cationic Charge for Diquats at pH = 2.5

| Derivatives | mg of Sample | ml of PVSK (turbidity) | ml of PVSK (Indicator) | meq/g (turbidity) | meq/g (indicator) |
| --- | --- | --- | --- | --- | --- |
| DQED | 3.72 | 12.0 | 11.5 | 0.66 | 0.64 |
| DQNNED | 3.67 | 14.5 | 16.3 | 0.66 | 0.91 |
| DQ13DAP | 3.99 | 15.0 | 14.0 | 0.81 | 0.72 |
| DQNNDAP | 3.61 | 12.5 | 10.0 | 0.72 | 0.57 |

(1) $N = 2.06 \times 10^{-4}$ eq/l; pH = 2.5
(2) Diquats prepared with 1% NaOH

For the polyquaternary ammonium cellulosics, titrating with PVSK proved to be effective. However, when analyzing the graft polycationic cellulosic, monoquats, and diquats, the use of sodium dodecyl sulfate ("SDS"), a twelve carbon anionic surfactant, was more effective for analyzing short chains grafts. After the less-bully SDS complexed with the first charge, the second charge was still accessible. Analysis of the cationic charge density for the graft polycationic cellulosics with SDS as titrant showed an average of one charge for the monoquats (Table 13), two charges for the diquats (Table 14), and five charges for the polyquats (Table 15). Analysis of the charge density with PVSK showed a general increase with quaternization for the monoquats and diquats, but was in close agreement with that of the polyquats. The agreement of charge density with the PVSK and SDS titrations for the polyquats suggested that the length of the cationic graft did influence the effectiveness of the polymer-polymer titration.

TABLE 13

Cationic Charge Density of Monoquats

| monoquats | SDS (meq/g) (turbidity) | PVSK (meq/g) (turbidity) | PVSK (meq/g) (indicator) |
| --- | --- | --- | --- |
| MQNNED | 0.97 | 0.11 | 0.11 |
| MQ13DAP | — | 0.25 | 0.31 |
| MQNNDAP | 1.26 | 0.40 | 0.38 |

SDS: $N = 2.03 \times 10^{-3}$ eq/l: PVSK: $N = 2.24 \times 10^{-4}$ eq/l (turbidity)
PVSK: $N = 1.49 \times 10^{-4}$ eq/l (indicator)

TABLE 14

Cationic Charge Density of Diquats*

| Diquats | SDS (meq/g) | PVSK (meq/g) (turbidity) | PVSK (meq/g) (Indicator) |
| --- | --- | --- | --- |
| DQNNED | 1.96 | 0.94 | 0.67 |
| DQ13DAP | 2.13 | 0.97 | 0.79 |
| DQNNDAP | 1.74 | 0.69 | 0.56 |

(1) SDS: $N = 2.03 \times 10^{-3}$ eq/l: PVSK: $N = 2.24 \times 10^{-4}$ eq/l (turbidity)
PVSK: $N = 1.49 \times 10^{-4}$ eq/l (indicator)
(2)* Diquats prepared from 10% NaOH.

TABLE 15

Cationic Charge Density of Polyquats

| Derivatives | SDS meq/g | PVSK (meq/g) Turbidity | PVSK (meq/g) Indicator |
| --- | --- | --- | --- |
| PQNNED |  | 3.84 | 4.68 |
| PQNNDAP | 4.44 | 4.40 | 3.75 |

TABLE 15-continued

Cationic Charge Density of Polyquats

| Derivatives | SDS meq/g | PVSK (meq/g) Turbidity | PVSK (meq/g) Indicator |
|---|---|---|---|
| PQNNED | 2.72 | 0.82 | 0.94 |
| PQNNDAP | 5.35 | 6.47 | 4.31 |

SDS: N = 2.03 × 10$^{-3}$ eq/l: PVSK: N = 2.24 × 10$^{-4}$ eq/l (turbidity)
PVSK: N = 1.49 × 10$^{-4}$ eq/l (indicator)

Viscosity. The diquats of the present invention have superior viscosity effects when compared to those of otherwise comparable monoquats, making them very useful in hair care gels, shampoos, conditioners, mousses, and the like in which a high viscosity is desired. For example, when dissolved in water alone at 25° C., a solution of the diquat DQNNED had a viscosity about 15 times higher than that of a solution of the monoquat MQNNED. When 10% to 50% ethanol was added to these aqueous solutions, the viscosity of the DQNNED solution changed little, while the viscosity of the MQNNED solution dropped to about one-third of its original value, or about 50 times lower than the viscosity of the aqueous alcohol solution of DQNNED.

Thus the novel diquats allow good rheological control of hair care and other cosmetic formulations, while using less polymer and less VOC's.

Bactericidal Properties. The novel polymers also have advantageous bactericidal properties. Samples of the polymer DQNNED were tested for bactericidal activity against E. coli. A measured amount of the initial inoculum of bacteria plated about 980,000 colonies, taken at the midpoint of the bacterial growth phase to insure that the E. coli were reproducing at or near their maximal rate. The polymer DQNNED was added to the medium to achieve a final concentration of 0.01 gram polymer per 100 mL of solution. The bacteria were incubated at 25° C. for 2 hours with the polymer, and were then plated. The same measured amount of inoculum then plated only about 60,000 colonies, a substantial reduction in bacterial count equivalent to a two-hour logarithmic (base 10) reduction rate of about 1.2 for E. coli. Samples plated at times much greater than 2 hours gave colony counts too low to measure accurately.

Experimental Procedures—General

Elemental analyses were conducted by Oneida Research Services, Inc. (Whitesboro, N.Y.). Nuclear Magnetic Resonance (NMR) analyses were performed using Bruker (San Jose, Calif.) AC100, 200AC and AM400 NMR instruments for $^1$H and $^{13}$C NMR. Seiko Instruments (Torrance, Calif.) DSC220C, TG/DTA 220, and DMS200 instruments were used to analyze the thermal properties of the derivatives. Infrared spectra were obtained with a Perkin Elmer (Norwalk, Conn.) 1700X series Fourier transform infrared (FTIR) spectrometer at 4 cm$^{-1}$ resolution and 10 to 25 scans. Intrinsic viscosities were measured in distilled water by standard procedures using a Ubbelohde dilution viscometer. Cone/plate viscosities were measured with a Brookfield Viscometer, CP #40. A UV-VIS-NIR Scanning Spectrometer was used to measure % transmittance and UV absorbance. A Spex (Edison, N.J.) Fluorescence Spectrometer was used to analyze fluorescence intensities. A Virtis-Freeze (Gardiner, N.Y.) Mobile 12XL was used for lyophilization. A Radiometer (Copenhagen, Denmark) PHM82, standard pH meter equipped with a combination electrode was used to monitor pH and conductivity.

Reagents and Solvents. Quat 188, 65% solution, was provided by Dow Chemical Company (Midland, Mich.).

All other reagents: cetylpyridinium chloride monohydrate (CPM); potassium polyvinylsulfate (PVSK); cyanoethylated cellulose (CEC); 6-(p-toluidino)-2-naphthalenesulfonic acid, potassium salt (TNS); 8-anilino-1-naphthalenesulfonic, ammonium salt (ANS); ethylene diamine; N,N-dimethylethylenediamine; 1,3-diaminopropane; N,N-dimethyldiaminopropane; N,N'-1,2-dimethylethylene diamine; 1,2diaminopropane; and iodomethane were purchased from Aldrich (Milwaukee, Wis.). These reagents were used without further purification.

Sodium dodecyl sulfate, 99% (SDS) was purchased from Sigma Chemical Co. (St. Louis, Mo.), and was used without further purification. Spectra/Por dialysis tubing, Spectrum Medical Industries Houston, Tex.) with a molecular weight cut off of 6,000–8,000 was used for lyophilization.

Preparation of Methyl Carboxymethyl Cellulose (MCMC). Commercially obtained sodium carboxymethylcellulose (10.35 g) was slurried in 20 ml of dimethyl sulfate for 1 day at room temperature. The crude reaction mixture was filtered, washed with copious amounts of water and methanol, and dried under vacuum. The MCMC ester (8.60 g, 83% conversion) was used without further purification in subsequent syntheses. $^1$H NMR (D$_2$O), δ (ppm): 3.1–4.4 (broad, overlapping peaks).

Preparation of Aminoalkylcarbamoylmethyl Cellulosics, Method One. Methyl carboxymethyl cellulose (1.10 g) was dissolved in excess RNH(CH$_2$)XNR'R" (20 ml) where R, R', R"=H or CH$_3$; and 0.2 g NH$_4$Cl was added. The reaction temperature was maintained at 90–100° C. for 1–5 hrs. The reaction mixture was cooled and dialyzed for 3 days against distilled water that was changed daily. The viscous crude mixture was freeze-dried. The product was redissolved in water, centrifuged, and relyophylized.

$^1$H NMR (D$_2$O) δ (ppm): 3.25–4.50 (broad peaks of anhydroglucose ring); CMCED δ: 2.95 (s), 3.05 (t), 3.30 (t); CMCNNED .5: 2.45 (s), 2.75 (overlapping triplets); CMC13DAP δ: 2.50 (p), 2.75 (t), 2.85 (t), 3.10 (t); CMCNNDAP δ: 2.50 (p), 2.70 (s), 2.60 (t), 2.75 (t), 2.85 (t), and 3.10 (t).

$^{13}$C NMR (D$_2$O) δ (ppm): 70–85 (C2, C3, C4, and C5 of anhydroglucose ring); CMCED δ: 104.6 (C1 of anhydroglucose ring), 54.6 (C6 of anhydroglucose ring), 45.6, 40.9, 37.5, carbonyl (unobserved); CMCNNED δ: 102.5 (C1 of anhydroglucose ring), 60.1 (C6 of anhydroglucose ring), 56.7, 56.1 ,43.6 ,43.2 ,35.9 ,34.4; 177.9 (amide carbonyl); CMC13DAP .6: 105.0 (C1 of anhydroglucose ring), 63.1 (C6 of anhydroglucose ring), 40.9, 37.4, 180.8 (carbonyl); CMCNNDAP 6: 102.5 (C1 of anhydroglucose ring), 56.2 (C6 of anhydroglucose ring), 43.9, 39.0, 38.3, 29.6, 25.3, 15.1, 177.8 (amide carbonyl).

FTIR (cm$^{-1}$), KBr pellets: CMCED, 3413 (s, O—H stretch), 2928 (w, C—H stretch), 1650 (amide I band, shoulder), 1592 (s, amide II band), 1125 and 1061 (vs, C—O—C stretch); CMCNNED, 3436 (s, O—H stretch), 2923 (w, C—H stretch), 1651 (amide I band, shoulder), 1593 (s, amide II band), 1113 and 1061 (s, C—O—C stretch); CMC13DAP, 3410 (s, O—H stretch), 2926 (w, C—H stretch), 1650 (amide I band, shoulder), 1591 (s, amide II band), 1112 and 1060 (s, C—O—C stretch); CMCNNDAP, 3195 (bs, O—H stretch), 2943 (w, C—H stretch), 1641 (s, amide band), 1058 (s, C—O—C stretch).

The degrees of substitution of the salt and the aminoamide cellulosics were determined by refluxing the dried derivatives in glacial acetic acid and conductrimetrically titrating with 0.1 N perchloric acid/dioxane solution. The degrees of substitution and the intrinsic viscosities were as follows:

CMC (DS=0.70), CMCED (DS=0.63, meq/g=3.07, η=1.56), CMCNNED (DS=0.57, meq/g=2.64, η=3.90), CMCNNDAP (DS=0.66, meq/g=2.81, η=1.08), CMC12DAP (DS=0.37, meq/g=2.02) and CMCSED (DS=0.35, meq/g=1.88). Elemental analysis: CMCNNED, Calculated 41.27% C; 4.65% N; Found 43.14% C; 4.57% N; CMCNNDAP, Calculated 43.25% C; 4.93% N; Found 44.09% C; 4.47% N.

Preparation of Aminoalkylcarbamoylmethyl Cellulosics, Method Two. The MCMC was slurried in diamine, $RNH(CH_2)_xNR'R''$, where R, R', R''=—H or —$CH_3$, and x=2 or 3, and this slurry was premixed for 3 days at room temperature. The reaction mixtures were then reacted at 90° C. for 1–3 days. The products were purified by dialysis for three days against distilled water, which was changed daily. Any undissolved particulates were removed by filtration. The filtered solutions were freeze-dried. The degrees of substitution of the CMC salt and of the aminoamide cellulosics were determined by refluxing the dried derivatives in glacial acetic acid and conductrimetrically titrating with 0.1 N perchloric acid/dioxane solution.

Reaction of Aminoamide Cellulosics with Epichlorohydrin (EPC). The aminoamides CMCED, CMCNNED, CMC13DAP, and CMCNNDAP, were separately slurried in 10 ml of EPC at 70° C. overnight. The reaction mixtures were cooled to room temperature, and washed with copious amounts of acetone. The products were dried overnight under vacuum. The solubilities of the derivatives were tested in distilled water and 1% NaOH. None of the derivatives was soluble in distilled water. The derivatives prepared from CMCNNED and CMCNNDAP dissolved in 1% NaOH after 3 days at room temperature.

$^1$H ($D_2O$) NMR δ (ppm): CMCNNED, 3.2–4.5 (broad, overlapping peaks of anhydroglucose ring); 3.0–3.5 (m, overlapping); 2.5–2.2 (t, t overlapping); 2.0 (t), 1.7 (s). CMCNNDAP, 3.2–4.5 (broad, overlapping peaks of anhydroglucose ring); 3.0 (t, overlapping peaks); 2.4 (t, overlapping peaks); 2.4 (s), 2.1 (s), 1.4 (m, broad).

Standardization of Perchloric Acid/Dioxane.

The titrant solution (0.1 N perchloric acid/dioxane) was prepared by adding 9 ml of perchloric acid to 1000 ml dioxane, and was stored in a brown bottle. A stock solution of potassium hydrogen phthalate ("KHP") was prepared by dissolving 2.5452 g KHP (dried at 120° C. overnight) in 250 ml glacial acetic acid. A 10 ml aliquot of this solution was placed in a 500 ml beaker with an additional 50 ml of glacial acetic acid. Titrations were carried out with continuous stirring, and the millivoltage was monitored with a combination electrode connected to a pH meter.

Determining the Degree of Substitution. The CMC salt, MCMC ester, and aminoamide cellulosics were separately dried at 110° C. for 2 days. The dried derivatives were suspended in 75 ml glacial acetic acid in a round bottom flask equipped with a stir bar and a water cooled condenser, and refluxed for 2.5 hours. The solutions were then poured into a 400 ml beaker with an additional 50 ml glacial acetic acid. The beaker was equipped with a stir bar and combination electrode. The solutions were titrated with 0.1N perchloric acid/dioxane solution with continuous stirring. The change in millivoltage was recorded from the pH meter.

Preparation of Quaternary Ammonium Salts. To a 25 ml or 50 ml round bottom flask equipped with a magnetic stir bar, aminoamide cellulosics (Method 2) were slurried in iodomethane. The solutions were continuously stirred for three days at room temperature. The products were purified by washing with copious amounts of acetone, and drying overnight in a vacuum oven. The dried products were yellow and water soluble. The degree of substitution was determined by titrating with SDS and PVSK.

Preparation of Diquaternary Ammonium Salts. The aminoamide cellulosics were dissolved in 10 ml of a 1% or 10% NaOH solution in a 25 ml or 50 ml round bottom flask equipped with a magnetic stirrer. Upon dissolution, 10 ml of Quat 188 was added to the reaction mixture, and the reaction was continued for 3 days at room temperature. The solutions were dialyzed for 3–5 days against distilled water, which was changed daily. The purified solutions were lyophilized. The degree of substitution was determined by titrating with SDS and PVSK.

$^1$H NMR ($D_2O$), δ (ppm): 3.25–4.5 (anhydroglucose ring, broad, overlapping peaks); DQED, 4.5 (m, broad), 3.6 (d), 3.5 (d,s overlapping), 3.2 (s,s); DQNNED, 4.5 (.mn, broad), 3.6 (d), 3.5–3.4 (d,s overlapping), 3.1 (s), 2.9 (s). DQ13DAP, 4.5 (m, broad), 3.6 (d), 3.5 (d,s overlapping), 3.4 (s, three), 1.9 (broad peak), DQNNDAP, 4.5 (m, broad), 3.6 (d), 3.4–3.5 (d,s overlapping), 3.3 (s), 3.2 (s), 3.1 (s), 2.8 (s, two), 1.9 (broad peak).

Preparation of Polyquaternary Ammonium Salts. CMCNNED (0.4396 g) was dissolved in 10 ml of dimethylamine (DMA), and 1.0 ml of epichlorohydrin (EPC) was then added dropwise in a three-neck round bottom flask equipped with a magnetic stir bar, thermometer, and reflux condenser. Upon addition of EPC, the temperature of the reaction rose initially to 50° C., but then dropped to 28° C. The mixture reacted overnight; the resultant viscous yellow solution was precipitated in acetone and dried under vacuum. The final product, PQNNED (0.9733 g) was gelatinous in appearance.

$^1$H NMR ($D_2O$) δ (ppm): 3.25–4.5 (broad, overlapping peaks of anhydroglucose ring), 3.5 (m, broad), 3.3–3.2 (d,d, broad, overlapping), 2.9–2.8 (d), 2.6 (s). $^{13}$C NMR ($D_2O$) δ (ppm): 70–85 (C2–C6, anhydroglucose ring), 105.1 (C1), 70.3, 69.3, 63.5, 62.1, 59.4, 56.2, 55.4, 45.9, 37.4, 176.0 (amide carbonyl). Elemental analysis of PQNNED: Calculated 35.81% C, 10.58% N; 21.57% Cl; Found 35.74% C, 10.56% N, 22.62% Cl.

CMCNNED (0.6100 g) was dissolved in 10 ml of dimethylamine (DMA) in a 3-neck, round bottom flask, equipped with a magnetic stir bar, water-cooled condenser, and thermometer. After the temperature dropped from 50° C., EPC (5 ml) was added, and the temperature rose to 100° C. After a few minutes the temperature dropped and the reaction mixture became gelatinous. After an hour, 50 ml of water was added and the product, PQNNED, was precipitated in copious amounts of acetone, and dried under vacuum.

CMCNNDAP (0.5356 g) was dissolved in 10.0 ml of dimethylamine ("DMA") and 5 ml of EPC in a three-neck round bottom flask equipped with a magnetic stir bar, thermometer, and reflux condenser. Upon addition of EPC, the temperature rose to 60° C., and the solution became very viscous. An additional 10 ml of DMA and 5 ml of EPC were added, and the reaction was allowed to proceed for 2 days. On day three, 5 ml of DMA was added, and the reaction was continued at room temperature. On day four, the product was purified by dialysis against distilled water for three days, and was then lyophilized. The final yield was 1.4063 g of product, PQNNDAP. $^1$H NMR ($D_2O$), δ (ppm): 3.2–4.5 (broad, overlapping peaks of anhydroglucose ring); 4.9 (m, broad, NH); 3.1–3.6 (d,d,s, broad, overlapping); 2.4–2.3 (m), 2.2 (s), 1.5. 13C NMR ($D_2O$), δ ppm): anhydroglucose ring (unobserved); 69.6, 64.3, 55.7 (m, broad); 47.3, 165.2

(amide carbonyl). Elemental analysis of PQNNDAP: Calculated 48.67% C, 9.08% N, 2.30% Cl; Found 49.61% C, 8.40% N, 2.36% Cl.

CMCNNDAP (0.1840 g) was dissolved in 10 ml of dimethylamine (DMA) in a 3-neck, round bottom flask, equipped with a magnetic stir bar, water-cooled condenser, and thermometer. After dissolution, EPC (1 ml) was added, and the temperature rose to 75° C. After a few minutes the temperature dropped and the reaction mixture became very viscous. Then 2 ml each of DMA and EPC were added daily for 3 days, and reaction continued at a temperature maintained between 40–50° C. The very viscous reaction mixture was dialyzed for 3 days against distilled water, and was then freeze-dried; 1.5747 g of product, PQNNDAP, was obtained. $^1$H NMR (D$_2$O), δ (ppm): 3.25–4.5 (broad overlapping peaks of anhydroglucose ring); 4.9 (s, broad); 3.6–3.4 (d,s,s overlapping); 3.3 (s), 3.2 (s).

Standardization of Potassium Polyvinylsulfate (PVSK) and Sodium Dodecyl Sulfate (SDS). Stock solutions of cetylpyridinium chloride monohydrate (CPM), 0.8010 g; potassium polyvinylsulfate (PVSK), 0.0405 g; and sodium dodecyl sulfate (SDS), 0.6837 g; respectively were prepared by dissolving in 1000 ml of distilled water. PVSK ($2.50 \times 10^4$ M), and SDS ($2.37 \times 10^{-3}$ M) solutions were used as the anionic titrants. SDS and PVSK, 25 ml aliquots, were standardized by $2.24 \times 10^{-3}$ M CPM using two drops of 1% toluidine blue indicator. The transmittance at 420 nm was measured with a spectrometer. During the titration, the solutions became cloudy and coagulated. The color changed from blue to purple, and at the endpoint to red-wine.

Differential Scanning Calorimetry ("DSC"). A Seiko DSC220C was used for thermal analysis of the aminoamide cellulosics. The glass transition temperature was observed after the aminoamide cellulosics were subjected to a cooling/heating cycle (25° C. to 125° C.) at 10° C./min. The aminoamides were also subjected to a cooling/heating cycle (125° C. to 500° C.) at a heating rate of 5° C./min to observe any other transitions. Both cooling/heating cycles were carried out in a nitrogen atmosphere.

Thermogravimetric Analysis ("TGA."). A Seiko TG/DTA 220 was used to observe the thermal stability of the aminoamide cellulosics. The derivatives were subjected to a two step analysis. The first heating cycle (25° C. to 130° C.) dried the cellulosics, and the second step (25° C. to 500° C.) was used to observe the thermal decomposition. The heating cycles were performed at 5° C./min in nitrogen.

Miscellaneous. The cellulosic derivatives of the present invention may be incorporated into hair care products of otherwise conventional formulation, but with lower levels of VOC's. For example a hairspray, in addition to the novel polymer, will typically contain plasticizers to give film flexibility and to modify adhesion, about 5% weight/volume, for example silicones, esters (e.g., isopropyl myristate), polyols (e.g., glycerol); softening agents, for example lanoline or lanoline derivatives; glossing agents to add shine, for example silicones; perfumes to cover the odor of the other components; solvents to spread the film and control drying rate, for example ethanol, isopropanol, or water; and propellants (about 40–70% of the total weight), for example butane, isobutane, or propane.

One example of a hairspray formulation follows: (1) polymer in accordance with the present invention, 1–4%; (2) lanolin, 0.05–0.25%; (3) silicone, 0.10–0.25.%; (4) isopropyl myristate, 0.05–0.50%; (5) perfume, 0.05–0.25%; (6) isopropanol, 10–50%; (7) isobutane, 40–70%.

When used as a thickener in gels, polymers in accordance with the present invention may be present between about 1% and about 20% by weight, preferably about 5%. The other components of a typical gel may for example be the following: polyethylene glycol, about 30%; isopropanol, about 25%; water, about 40%.

These formulations work well with VOC levels below about 30%, compared to current formulations that typically use up to 50% VOC's. As the novel polymers are water soluble, it would also be possible to use water as the sole solvent, without any VOC's, if desired. However, drying times for the formulations would be adversely affected. Even if VOC's are used, the levels are substantially lower than is required for currently used compounds. Even 10% ethanol greatly reduces the drying time of a formulation.

Typical components of shampoos include surfactants, foam boosters, conditioning agents, preservatives, sequestering agents, polymeric viscosity modifiers, opacifying or clarifying agents, water, fragrance, coloring agents, stabilizers (e.g., antioxidants, ultraviolet absorbers), and optional specialty additives. One example of a shampoo formulation using the compounds of the present invention follows: sodium lauryl sulfate, about 10%; lauric diethanolamide, about 5%; hexylene glycol, about 3%; methyl p-hydroxy benzoate, about 0.1%; sodium chloride; stearic acid or boric acid, about 1%; cationic cellulosic derivative, about 0.5%; ethanol, about 15%; water to 100%.

Another example of a shampoo formulation in accordance with the present invention, a 2-in-1 conditioning shampoo, is the following: coconut amidopropyl-3-dimethylamino betaine, about 5.5%; sodium laurel sulfate, about 5%; ethanol, about 15%; cationic cellulose polymer, about 1%; perfume, about 0.5%; methyl-p-hydroxybenzoate (preservative), about 0.25%; antioxidant, about 0.25%; EDTA (sequestering agent), about 0.05%; water, to 100%.

Other uses for the novel polymers include conditioners, mousses, spritzes, hot oil treatments, detanglers, conditioning hair masks, hair colors, permanent wave products, and leave-in conditioners. The polymers may be used in formulations that are otherwise in accordance with formulations known in the art, preferably with lower levels of VOC's. See, e.g., J. B. Wilkinson et al. (eds.), *Harry's Cosmeticology*, Chem. Publishing, New York (1982).

The complete disclosures of all references cited in this specification are hereby incorporated by reference. In the event of an otherwise irreconcilable conflict, however, the present specification shall control.

We claim:

1. A method for killing bacteria or inhibiting the growth of bacteria, comprising applying to the bacteria a carboxymethyl cellulose derivative, wherein some or all of the sites normally occupied by carboxymethyl groups are occupied by diquaternary ammonium groups of the formula

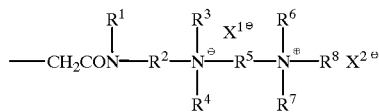

wherein there are at least about 0.2 said diquaternary ammonium groups present for each anhydroglucose unit of said cellulose derivative; and wherein:

$R^1$ is hydrogen or methyl;

$R^2$ is a divalent aliphatic hydrocarbon group with 2 to 20 carbon atoms;

$R^3, R^4, R^6, R^7$, and $R^8$ are alkyl groups with 1 to 4 carbon atoms that may be the same as one another or different from one another;

$R^5$ is a substituted or unsubstituted divalent aliphatic group with 2 to 5 carbon atoms; and $X^1$ and $X^2$ are anions that may be the same as one another or different from one another.

2. A method as recited in claim 1, wherein there are between about 0.3 and about 0.7 said diquaternary ammonium groups present for each anhydroglucose unit of said cellulose derivative; and wherein:

$R^1$ is hydrogen;

$R^2$ is —$CH_2$—$CH_2$— or —$CH_2$—$CH_2$—$CH_2$—;

$R^3$, $R^4$, $R^6$, $R^7$, and $R^8$ are each methyl groups;

$R^5$ is —$CH_2$—CH(OH)—$CH_2$—; and $X^1$ and $X^2$ are may be the same as one another or different from one another, and are each a halide, a sulfate ester group, or a sulfonic acid group.

3. A method as recited in claim 2, wherein there are about 0.5 said diquaternary ammonium groups present for each anhydroglucose unit of said cellulose derivative; wherein $R^2$ is —$CH_2$—$CH_2$—; and wherein $X^1$ and $X^2$ are each chloride.

4. A method for killing bacteria or inhibiting the growth of bacteria, comprising applying to the bacteria a carboxymethyl cellulose derivative, wherein some or all of the sites normally occupied by carboxymethyl groups are occupied by polyquaternary ammonium groups of the formula

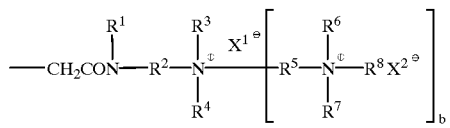

wherein there are at least about 0.2 said diquaternary ammonium groups present for each anhydroglucose unit of said cellulose derivative; wherein b is between 2 and 8; and wherein:

$R^1$ is hydrogen or methyl;

$R^2$ is a divalent aliphatic hydrocarbon group with 2 to 20 carbon atoms;

$R^3$, $R^4$, $R^6$, $R^7$, and $R^8$ are alkyl groups with 1 to 4 carbon atoms that may be the same as one another or different from one another;

$R^5$ is a substituted or unsubstituted divalent aliphatic group with 2 to 5 carbon atoms; and $X^1$ and $X^2$ are anions that may be the same as one another or different from one another.

5. A method as recited in claim 4, wherein there are between about 0.3 and about 0.7 said diquaternary ammonium groups present for each anhydroglucose unit of said cellulose derivative; wherein b is 4 or 5; and wherein:

$R^1$ is hydrogen;

$R^2$ is —$CH_2$—$CH_2$— or —$CH_2$—$CH_2$—$CH_2$—;

$R^3$, $R^4$, $R^6$, $R^7$, and $R^8$ are each methyl groups;

$R^5$ is —$CH_2$—CH(OH)—$CH_2$—; and $X^1$ and $X^2$ are may be the same as one another or different from one another, and are each a halide, a sulfate ester group, or a sulfonic acid group.

6. A method as recited in claim 5, wherein there are about 0.5 said diquaternary ammonium groups present for each anhydroglucose unit of said cellulose derivative; wherein b is 4; wherein $R^2$ is —$CH_2$—$CH_2$—; and wherein $X^1$ and $X^2$ are each chloride.

* * * * *